United States Patent
Nakamura

(10) Patent No.: US 10,514,327 B2
(45) Date of Patent: Dec. 24, 2019

(54) AUTOSAMPLER

(71) Applicant: SHIMADZU CORPORATION, Kyoto-shi, Kyoto (JP)

(72) Inventor: Takafumi Nakamura, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 181 days.

(21) Appl. No.: 15/652,528

(22) Filed: Jul. 18, 2017

(65) Prior Publication Data

US 2019/0025161 A1    Jan. 24, 2019

(51) Int. Cl.
*G01N 1/14* (2006.01)
*G01N 30/24* (2006.01)
*G01N 30/02* (2006.01)

(52) U.S. Cl.
CPC .............. *G01N 1/14* (2013.01); *G01N 30/24* (2013.01); *G01N 2001/1427* (2013.01); *G01N 2030/027* (2013.01)

(58) Field of Classification Search
CPC .. G01N 1/14; G01N 30/24; G01N 2001/1427; G01N 2030/027
USPC ....................................... 73/863.01
See application file for complete search history.

(56) References Cited

U.S. PATENT DOCUMENTS

| 4,713,974 A * | 12/1987 | Stone | G01N 30/24 422/64 |
| 2005/0194318 A1* | 9/2005 | Ozbal | B01F 5/0085 210/656 |
| 2006/0153716 A1* | 7/2006 | Shoji | B01L 3/50255 417/442 |
| 2007/0137320 A1* | 6/2007 | Bremer | G01N 30/18 73/864.01 |
| 2010/0024527 A1* | 2/2010 | LaMarr | G01N 30/24 73/61.56 |
| 2010/0206411 A1* | 8/2010 | Maeda | F16K 11/074 137/625.17 |
| 2010/0237235 A1* | 9/2010 | Ozbal | G01N 30/24 250/282 |
| 2010/0288025 A1 | 11/2010 | Hochgraeber | |

(Continued)

FOREIGN PATENT DOCUMENTS

| JP | 2001-255316 A | 9/2001 |
| JP | 2005-265805 A | 9/2005 |

OTHER PUBLICATIONS

Communication dated Apr. 17, 2018 issued by the Japanese Patent Office in counterpart application No. 2015-011913.

*Primary Examiner* — Natalie Huls
*Assistant Examiner* — Mohammed E Keramet-Amircolai
(74) *Attorney, Agent, or Firm* — Sughrue Mion, PLLC

(57) ABSTRACT

An autosampler includes a pressure release operation unit for performing, by controlling operation of a needle drive mechanism and a switching mechanism, before a tip end of a needle is pulled out from an injection port following a state where a sampling channel is disposed between a feeding device and an analytical column, a pressure release operation of switching the switching mechanism in such a way that the sampling channel is not disposed between the feeding device and the analytical column and a system including the sampling channel is made an open system, and of performing standby until a pressure inside the sampling channel is returned to atmospheric pressure.

5 Claims, 6 Drawing Sheets

(56) References Cited

U.S. PATENT DOCUMENTS

| | | | |
|---|---|---|---|
| 2010/0326215 A1* | 12/2010 | Maeda | G01N 30/20 73/864.21 |
| 2011/0209532 A1* | 9/2011 | Maeda | G01N 30/24 73/61.56 |
| 2012/0024048 A1* | 2/2012 | Maeda | G01N 30/20 73/61.55 |
| 2013/0014566 A1* | 1/2013 | Marks | G01N 30/24 73/61.55 |
| 2013/0067997 A1* | 3/2013 | Ebsen | G01N 30/20 73/61.55 |
| 2015/0226710 A1* | 8/2015 | Hochgraeber | G01N 30/18 73/61.55 |
| 2015/0377843 A1* | 12/2015 | Morikawa | G01N 30/24 73/863.02 |

* cited by examiner

At The Time of Pressure Release

At The Time of Sampling

AUTOSAMPLER

BACKGROUND OF THE INVENTION

1. Field of the Invention

The present invention relates to an autosampler for introducing a sample into an analysis channel of a liquid chromatograph.

2. Description of the Related Art

As an autosampler, of a liquid chromatograph, for automatically collecting a sample and for introducing the sample into an analysis channel, there is an autosampler which includes a sampling channel including a needle for collecting a sample and a sample loop for retaining the collected sample, a syringe pump for suctioning a sample through the needle, a feeding device for feeding a mobile phase, and a switching valve including a plurality of ports to which respective analysis channels communicating with an analytical column and a detector are connected, where switching of a channel structure is performed by the switching valve (see JP 2005-265805 A). An injection port to which the sampling channel is connected by insertion of a needle tip end is provided to the switching valve.

The switching valve of such an autosampler is configured to switch whether the sampling channel is disposed between the feeding device and the analytical column or not, when the needle tip end is inserted in the injection port.

At the time of collection of a sample, the sampling channel is not disposed between the feeding device and the analytical column, the sampling channel and the syringe pump are communicated with each other, the needle tip end is inserted into a sample container, and the syringe pump is driven to perform suction so that a sample is suctioned from the needle tip end and is retained inside the sample loop.

At the time of introduction, into the analysis channel, of the sample collected by the sampling operation described above, the needle tip end is inserted into the injection port and the switching valve is switched in such a way that the sampling channel is disposed between the feeding device and the analytical column, and the sample retained in the sample loop is introduced into the analysis channel by a mobile phase from the feeding device. The sample which is introduced into the analysis channel is separated into components at the analytical column, and detection is performed by the detector.

According to the autosampler described above, in a case of suctioning a sample by moving the needle to the sample container, if the needle tip end is inserted in the injection port at an immediately preceding time point and the sampling channel is disposed between the feeding device and the analytical column, the mobile phase from the feeding device has been fed through the sampling channel at a high pressure, and thus, a compressed mobile phase is present in the sampling channel. If the needle is pulled out from the injection port in this state, the mobile phase is ejected from the tip end of the needle, and problems such as the inside of the device being contaminated may occur

SUMMARY OF THE INVENTION

Accordingly, the present invention has an object to prevent ejection of a liquid from a needle tip end at the time a needle being pulled out from an injection port.

An aspect of an autosampler according to the present invention includes a sampling channel, a needle drive mechanism, an injection port, a switching mechanism, and a pressure release operation unit. The sampling channel includes, at one end, a needle for suctioning a sample from a sample container containing a sample, and includes a sample loop for retaining the sample suctioned through the needle. The needle drive mechanism is for moving the needle. The injection port is connected to the sampling channel by insertion of a tip end of the needle. The switching mechanism switches, when the tip end of the needle is inserted in the injection port, to one of a state where the sampling channel is disposed between a feeding device for feeding a mobile phase and an analytical column for separating a sample into components and a state where the sampling channel is not disposed between the feeding device and the analytical column. The switching mechanism also switches, when in a state where the sampling channel is not disposed between the feeding device and the analytical column, a system including the sampling channel between an open system and a closed system. The pressure release operation unit performs, by controlling operation of the needle drive mechanism and the switching mechanism, before the tip end of the needle is pulled out from the injection port following a state where the sampling channel is disposed between the feeding device and the analytical column, a pressure release operation of switching the switching mechanism in such a way that the sampling channel is not disposed between the feeding device and the analytical column and the system including the sampling channel is made the open system, and of performing standby until a pressure inside the sampling channel is returned to atmospheric pressure.

According to an aspect of the autosampler according to the present invention, the pressure release operation unit is provided, which is for performing, by controlling operation of the needle drive mechanism and the switching mechanism, before the tip end of the needle is pulled out from the injection port following a state where the sampling channel is disposed between the feeding device and the analytical column, a pressure release operation of switching the switching mechanism in such a way that the sampling channel is not disposed between the feeding device and the analytical column and the system including the sampling channel is made the open system, and of performing standby until a pressure inside the sampling channel is returned to atmospheric pressure. Therefore the pressure inside the sampling channel is returned to atmospheric pressure before the tip end of the needle is pulled out from the injection port, and a mobile phase may be prevented from being ejected from the tip end of the needle when the tip end of the needle is pulled out from the injection port.

DETAILED DESCRIPTION OF THE INVENTION

Figure 1:
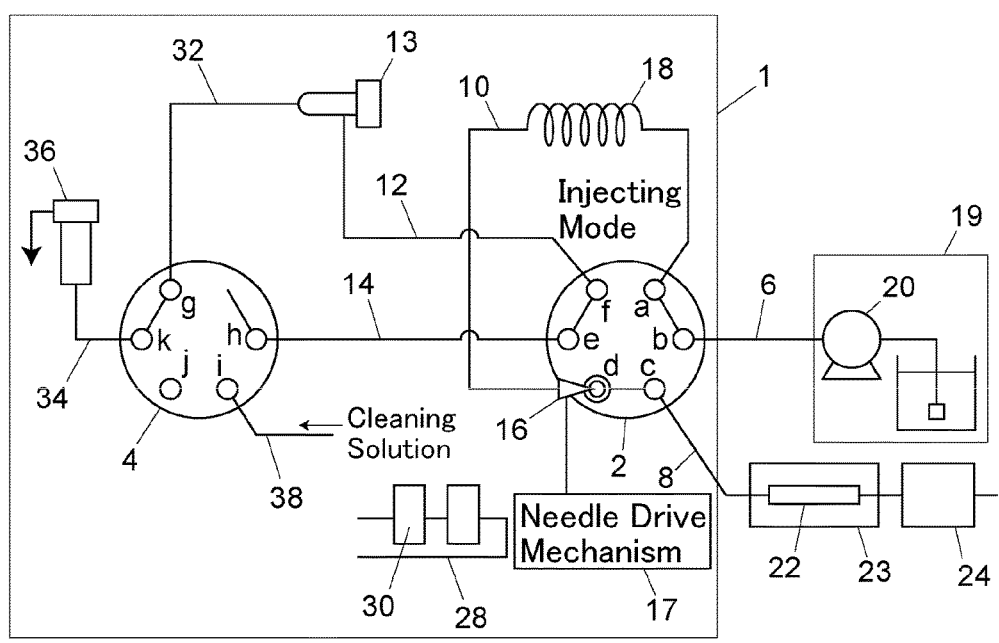
FIG. 1 is a channel configuration diagram of a liquid chromatograph including an autosampler according to an embodiment.

The time required for the pressure inside a sampling channel to be returned to atmospheric pressure by a pressure release operation differs depending on the pressure inside the sampling channel immediately preceding the pressure release operation. If the pressure inside the sampling channel is high, a long time is required for the pressure inside the sampling channel to be returned to atmospheric pressure. If the pressure inside the sampling channel is low, the pressure inside the sampling channel may be returned to atmospheric pressure in a short time. If, in spite of the above facts, the pressure release operation is performed for a uniform period of time, the pressure release operation is possibly performed for longer than necessary, and the analysis efficiency is reduced in such a case.

Accordingly, a pressure release time setting unit for setting an execution time of the pressure release operation based on a feed pressure of a feeding device for a mobile phase immediately before execution of the pressure release operation is further provided. A pressure release operation unit preferably performs the pressure release operation for a period of time set by the pressure release time setting unit. This allows the time required for the pressure release operation to be according to the immediately preceding pressure inside the sampling channel, and the analysis efficiency may be increased.

As a preferred embodiment of the above-described case, a pressure release time information holding unit holding pressure release time information specifying in advance a relationship between the feed pressure and the execution time of the pressure release operation is further provided. The pressure release time setting unit captures the feed pressure of the feeding device before the pressure release operation is performed, and sets the execution time of the pressure release operation based on the captured feed pressure and the pressure release time information that is held in the pressure release time information holding unit.

Furthermore, in addition to a control unit for controlling a needle drive mechanism and a switching mechanism, a system controller for communicating information with the control unit may be provided. In such a case, the pressure release time setting unit may be provided in the system controller.

The switching mechanism may include two switching valves. In this case, a first switching valve as one of the switching valves may include a sampling port to which another end of the sampling channel is connected, a syringe port to which a syringe pump for performing suction and discharge of liquid is connected, an injection port, a mobile phase supply port to which the feeding device for supplying a mobile phase is connected, and an analysis port to which a channel communicating with an analytical column is connected. The switching mechanism switches between a loading mode in which the sampling port and the syringe port are connected and the mobile phase supply port and the analysis port are connected, and an injecting mode in which the sampling port and the mobile phase supply port are connected and the injection port and the analysis port are connected. A second switching valve as the other switching valve switches a system including a sampling channel which is formed when a tip end of a needle is inserted in the injection port and the first switching valve is in the loading mode, between an open system and a closed system.

Hereinafter, an embodiment of an autosampler according to the present invention will be described with reference to the drawings.

First, a liquid chromatograph provided with the autosampler according to the embodiment will be described with reference to FIG. 1.

The liquid chromatograph includes an autosampler 1, a feeding device 19, an analytical column 22, and a detector 24. The autosampler 1 is provided with a first switching valve 2 and a second switching valve 4 as a switching mechanism for switching a channel configuration of the liquid chromatograph.

The first switching valve 2 is a high pressure rotary valve comprising six ports. The first switching valve 2 comprises six ports: a port "a" (sampling port) to which a sampling channel 10 is connected, a port "b" (mobile phase supply port) to which a mobile phase feeding channel 19 is connected, a port "c" (analysis port) to which an analysis channel 8 communicating with one end of the analytical column 22 is connected, an injection port "d", a port "e" to which a channel 14 communicating with a port "h" of the second switching valve 4, described below, is connected, and a port "f" (syringe port) to which a syringe channel 12 communicating with a syringe pump 13 is connected.

The second switching valve 4 includes ports "g", "h", "i", "j", and "k". Of these ports, the port "g" is connected to the syringe pump 13 via a syringe channel 32, the port "h" is connected to the port "e" of the first switching valve 2 via the channel 14, and the port "k" is connected to a cleaning port 36 via a channel 34. Furthermore, a channel 38 for supplying a cleaning solution is connected to the port "i".

The feeding device 19 includes a feed pump 20, and feeds a mobile phase to the autosampler 1 through a mobile phase supply channel 6. The other end of the analytical column 22 is connected to the detector 24 through a pipe. The analytical column 22 is accommodated inside a column oven 23, and its temperature is controlled to be constant.

The sampling channel 10 includes a needle 16 for sampling at a distal end, and also, includes a sample loop 18 for retaining a sample suctioned in through the tip end of the needle 16. The needle 16 is moved in a horizontal direction and a vertical direction by a needle drive mechanism 17, and accesses the injection port d of the first switching valve 2 or a sample container 30 installed in a sample rack 28.

The syringe pump 13 includes two suction/discharge ports, and the syringe channel 12 is connected to one of the suction/discharge ports, and the channel 32 is connected to the other of the suction/discharge ports. The channel 32 for cleaning is connected to the port "g" of the second switching valve 4.

In the first switching valve 2, the port "a" is adjacent to the ports "b" and "f", the port "c" is adjacent to the ports "c" and "d", and the port "e" is adjacent to the ports "d" and "f". The first switching valve 2 switches connection between adjacent ports, and switching is performed between a state where the ports "a" and "b", "c" and "d", and "e" and "f" are connected (the state shown in FIG. 1; hereinafter referred to as an injecting mode) and a state where the ports "a" and "f", "b" and "c", and "d" and "e" are connected (the state shown in FIGS. 5 and 6; hereinafter referred to as a loading mode).

The second switching valve 4 is switched at the time of suction of a sample, at the time of suction/discharge of a cleaning solution, and at the time of pressure release at the sampling channel 10.

At the time of suction of a sample from the sample container 30, the second switching valve 4 is placed in a state where the ports "g" and "k" are not communicated with each other. At this time, the first switching valve 2 is placed in the loading mode and the ports "a" and "f" are communicated with each other, and thus, the syringe pump 13 is communicated with the tip end of the needle 16, and the syringe pump 13 is enabled to suction a sample through the needle 16 (see FIG. 6).

At the time of suction/discharge of a cleaning solution, first, the ports "i" and "h" of the second switching valve 4 are communicated with each other, and the first switching valve 2 is placed in the injecting mode and the ports "e" and "f" are communicated with each other, and thus, the syringe pump 13 and the channel 38 for supplying a cleaning solution are communicated with each other. By driving the syringe pump 13 in this state to perform suction, a cleaning solution is suctioned into the syringe pump 13. Then, at the second switching valve 4, the ports "g" and "k" are communicated with each other and the port "h" is closed, and the cleaning solution is discharged from the syringe pump 13, and thus, the cleaning solution is fed to the cleaning port 36 through the channel 32 for cleaning and the channel 34.

In the case of releasing the pressure inside the sampling channel 10, the ports "g" and "k" are communicated with each other and the port "h" is closed at the second switching valve 4. At this time, the first switching valve 2 is placed in the loading mode and the ports "a" and "d" are communicated with "f" and "e", respectively, and thus, the sampling channel 10 is communicated with the cleaning port 36, which is opened to the atmosphere, and the pressure inside the sampling channel 10 is reduced to atmospheric pressure over time (see FIG. 5).

An example of a control system according to the embodiment will be described with reference to FIG. 2.

The autosampler 1, the feeding device 19, the column oven 23, and the detector 24 are connected to a common system controller 48, and operation is managed by the system controller 48 in a centralized manner. Additionally, a general-purpose personal computer may be used instead of the system controller 48.

Figure 2:
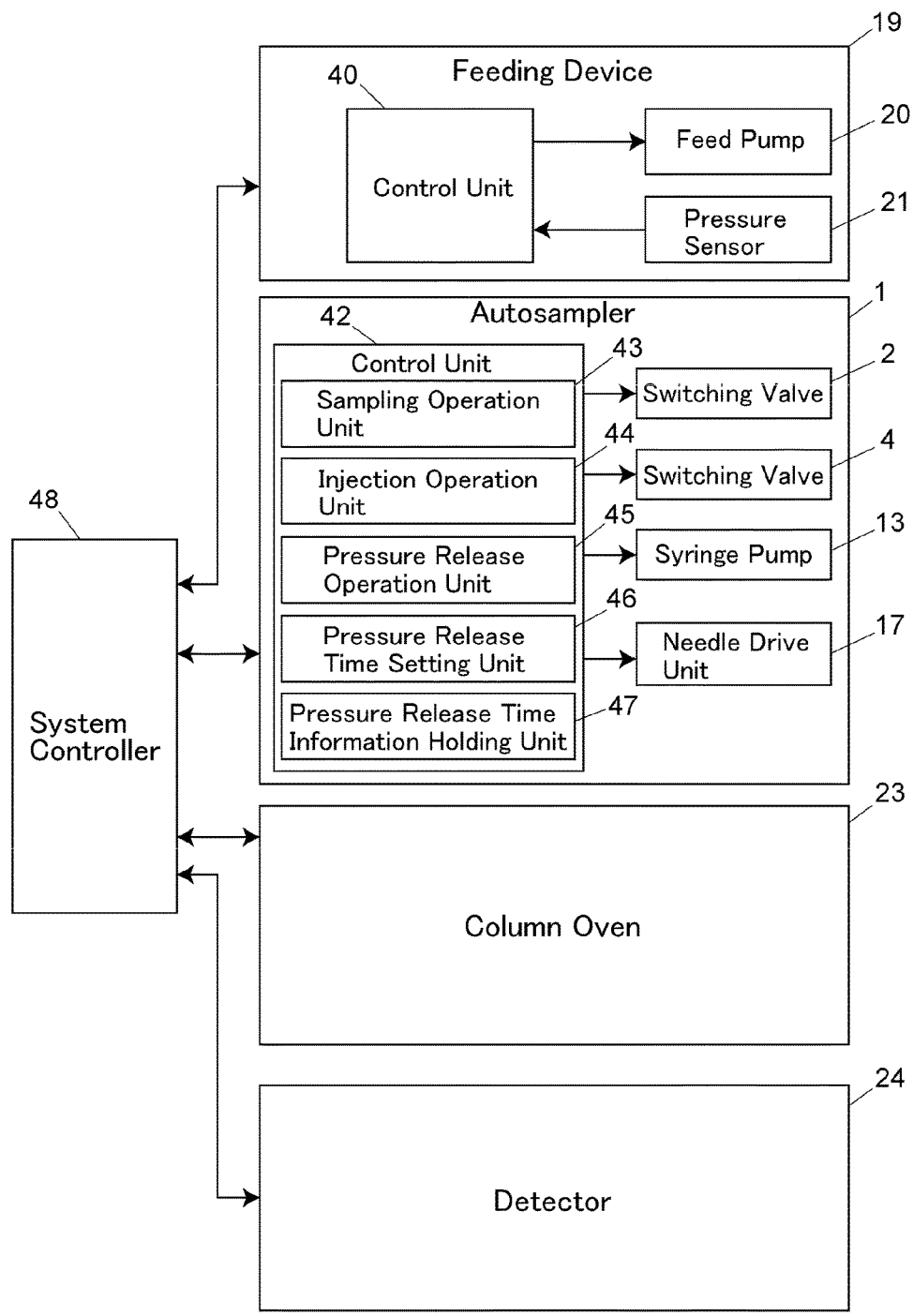
FIG. 2 is a block diagram showing an example of a control system according to the embodiment.

The autosampler 1, the feeding device 19, the column oven 23, and the detector 24 each include a control unit for controlling operation of respective operation modules, but in FIG. 2, only a control unit 40 of the feeding device 19 and a control unit 42 of the autosampler 1 are shown, and other control units are omitted from the drawing. The control unit provided to each of the autosampler 1, the feeding device 19, the column oven 23, and the detector 24 communicates information with the system controller 48, and supplies a signal based on information provided by the system controller 48 to each module. Such a control unit is realized by a combination of an arithmetic processing device, such as a CPU, and a storage device storing a predetermined program.

The control unit 40 controls operation of the feed pump 20 in such a way that a mobile phase is fed at a flow rate that is set in advance. The feeding device 19 is provided with a pressure sensor 21 (omitted from FIG. 1) for detecting a feed pressure for the mobile phase.

At the autosampler 1, the control unit 42 for controlling operation of the first switching valves 2, 4, the syringe pump 13, and the needle drive unit 17 includes a sampling operation unit 43, an injection operation unit 44, a pressure release operation unit 45, a pressure release time setting unit 46, and a pressure release time information holding unit 47. The sampling operation unit 43, the injection operation unit 44, the pressure release operation unit 45, and the pressure release time setting unit 46 are functions that are realized by an arithmetic processing device executing programs stored in a storage device constituting the control unit 42. The pressure release time information holding unit 47 is a storage region provided in the storage device constituting the control unit 42.

The sampling operation unit 43 is configured to perform a sampling operation of suctioning a sample from the tip end of the needle 16 and retaining the sample in the sample loop 18, according to a signal for sampling operation start supplied from the system controller 48. In the sampling operation, the first switching valve 2 is placed in the loading mode and the sampling channel 10 and the syringe channel 12 are connected, and the second switching valve 4 is rotated 30 degrees and the ports "g" and "k" are cut off from each other (closed system), and then, the tip end of the needle 16 is inserted into the sample container 30 and the syringe pump 13 is driven in a suction direction so that a sample inside the sample container 30 is suctioned from the tip end of the needle 16 (see FIG. 6).

The injection operation unit 44 is configured to perform an injection operation of introducing, into the analysis channel 8, the sample held in the sample loop 18 by the sampling operation described above. After the sampling operation described above, the injection operation 44 inserts the tip end of the needle 16 into the injection port "d" of the first switching valve 2, switches the first switching valve 2 to the loading mode and achieves a state where the sampling channel 10 is connected between the mobile phase supply channel 6 and the analysis channel 8, as shown in FIG. 1, and introduces the sample held in the sample loop 18 into the analysis channel 8 by a mobile phase from the feeding device 19.

The pressure release operation unit 45 is configured to perform, before the needle 16 is pulled out from the injection port "d", such as before execution of the sampling operation described above, a pressure release operation of returning the pressure inside the sampling channel 10 to atmospheric pressure. In many cases, the needle 16 is inserted in the injection port "d" of the first switching valve 2 until immediately before execution of the sampling operation, and a mobile phase is flowing through the sampling channel 10 from the feeding device 19 (state shown in FIG. 1). In the case of subsequently performing the sampling operation, the first switching valve 2 is switched to the loading mode, and the needle 16 is moved to the sample container 30 to achieve the state shown in FIG. 6, but if the needle 16 is pulled out from the injection port "d" immediately after the first switching valve 2 is switched to the loading mode, liquid may be ejected from the needle 16 due to the pressure inside the sampling channel 10 being at the feed pressure of the feeding device 19.

Figure 5:
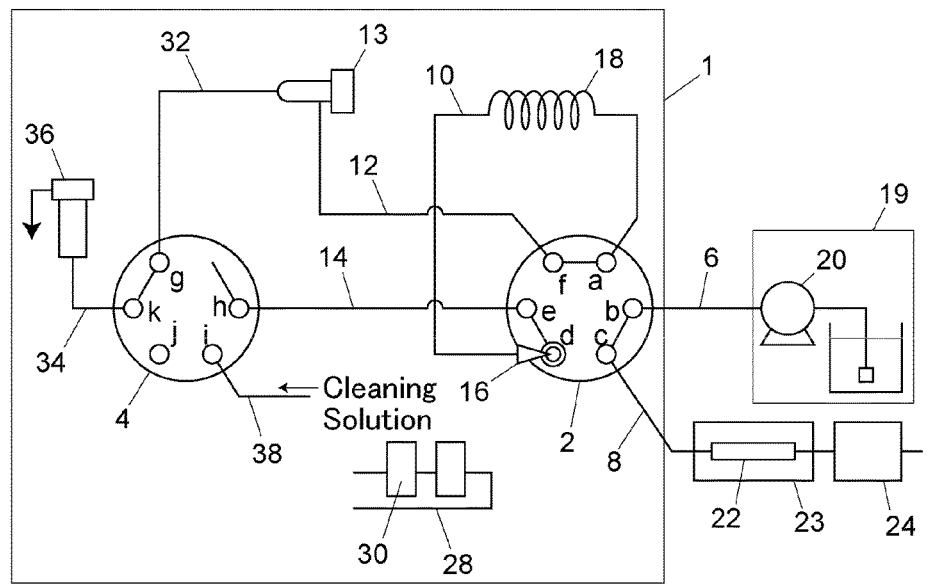
FIG. 5 is a channel configuration diagram at the time of a pressure release operation according to the embodiment.

Accordingly, as the pressure release operation, before the needle 16 is pulled out from the injection port "d", the second switching valve 4 is placed in a state where the ports "g" and "k" are connected, as shown in FIG. 5, and also, the first switching valve 2 is switched to the loading mode, and standby is performed for a period of time set in advance as a pressure release time. As described above, in the state shown in FIG. 5, the sampling channel 10 is communicated with the cleaning port 36, which is opened to the atmosphere, through the syringe channel 12, the syringe pump 13, the cleaning channel 32, and the channel 34, and the pressure inside the sampling channel 10 is released over time to return to atmospheric pressure.

The atmospheric air release time setting unit 46 is configured to set the execution time of the pressure release operation described above, that is, the time of standby in the state shown in FIG. 5 (pressure release time). The time from the state shown in FIG. 5 being achieved to the pressure inside the sampling channel 10 returning to atmospheric pressure is determined by the pressure inside the sampling channel 10 immediately before the channel configuration is switched to the state shown in FIG. 5, that is, the immediately preceding feed pressure of the feeding device 19. The correlation between the feed pressure of the feeding device 19 and the time required for the pressure inside the sampling channel 10 to return to atmospheric pressure is experimentally determined in advance, and correlation data is prepared in the pressure release time information holding unit 47 as pressure release time information. The atmospheric air release time setting unit 46 sets the pressure release time based on the feed pressure of the feeding device 19 and the atmospheric air release time information held in the atmospheric air release time information holding unit 47.

Figure 3:
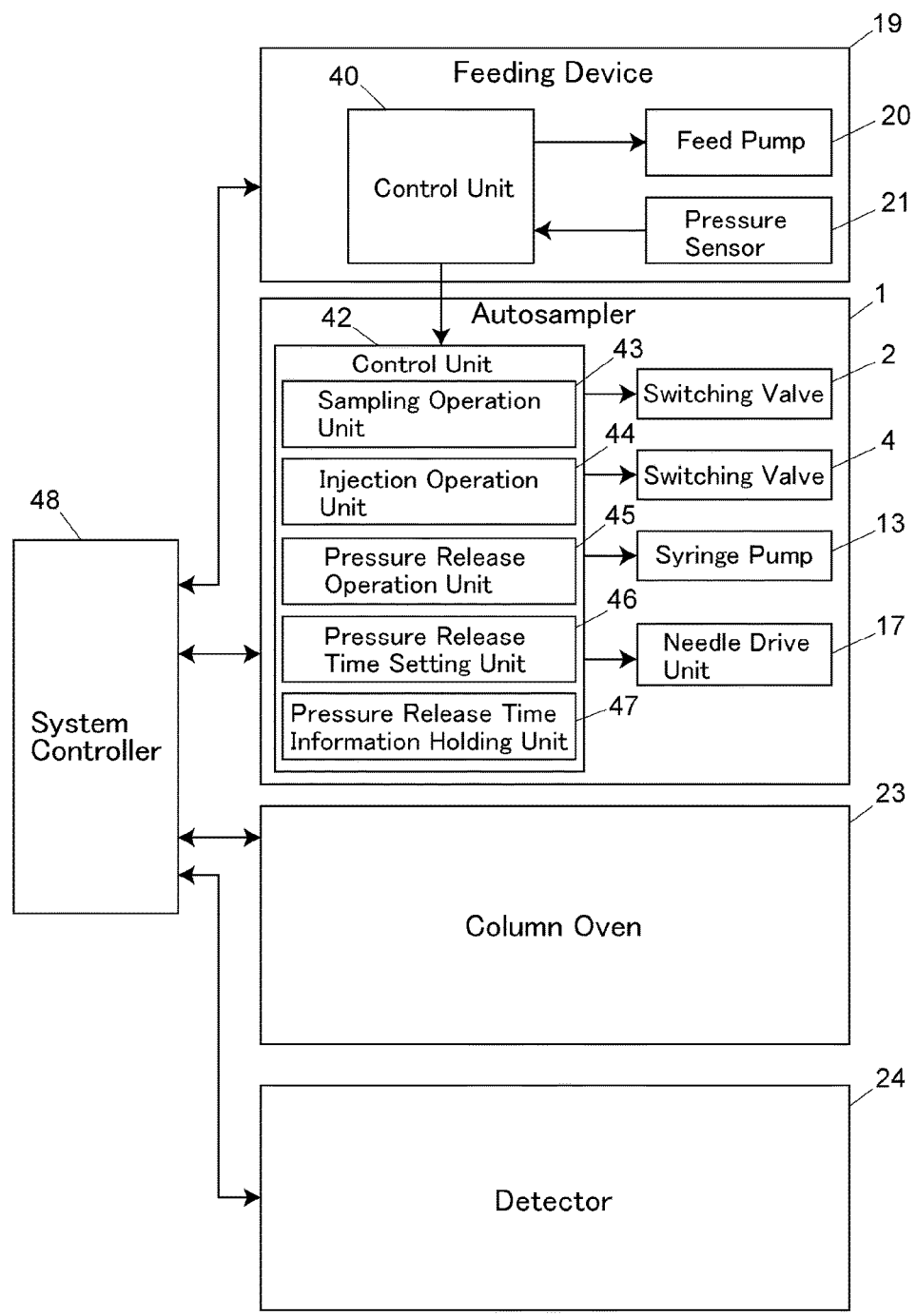
FIG. 3 is a block diagram showing another example of the control system according to the embodiment.

Additionally, information about the feed pressure of the feeding device 19 may be captured by the control unit 42 from the system controller 48, or as shown in FIG. 3, may be captured by the control unit 42 from the control unit 40 of the feeding device 19.

Figure 7:
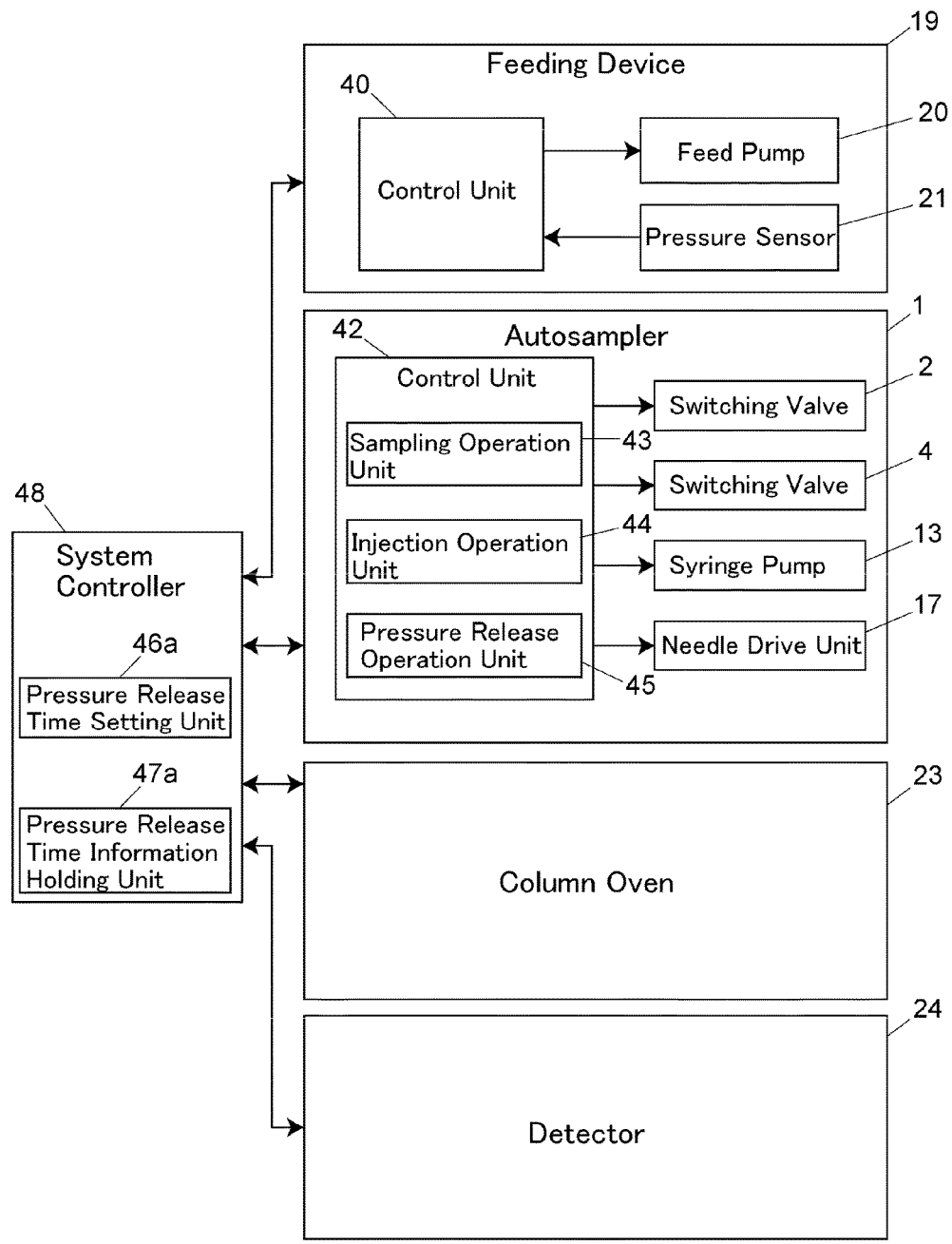
FIG. 7 is a block diagram showing further another example of the control system according to the embodiment.

As shown in FIG. 7, functions for setting the pressure release time according to the feed pressure of the feeding device 19 (pressure release time setting unit 46a, pressure release time information holding unit 47a) may be provided to the system controller 48. Alternatively, the functions may be provided to the feeding device 19.

The atmospheric air release time setting unit 46 may set the atmospheric air release time by further taking into account the inner diameter or the length of the sample loop 18, the type of a mobile phase (rate of compression, viscosity, etc.) or the like. In this case, correlation between the time required for the pressure inside the sampling channel 10 to return to atmospheric pressure and the inner diameter or the length of the sample loop 18 or the type of a mobile phase is also prepared in the atmospheric air release time information holding unit 47 as the atmospheric air release time information, and the atmospheric air release time setting unit 46 sets the atmospheric air release time based on the feed pressure of the feeding device, information, supplied by the system controller 48, about the inner diameter or the length of the sample loop 18 or about the type of a mobile phase, and the atmospheric air release time information.

Figure 4:
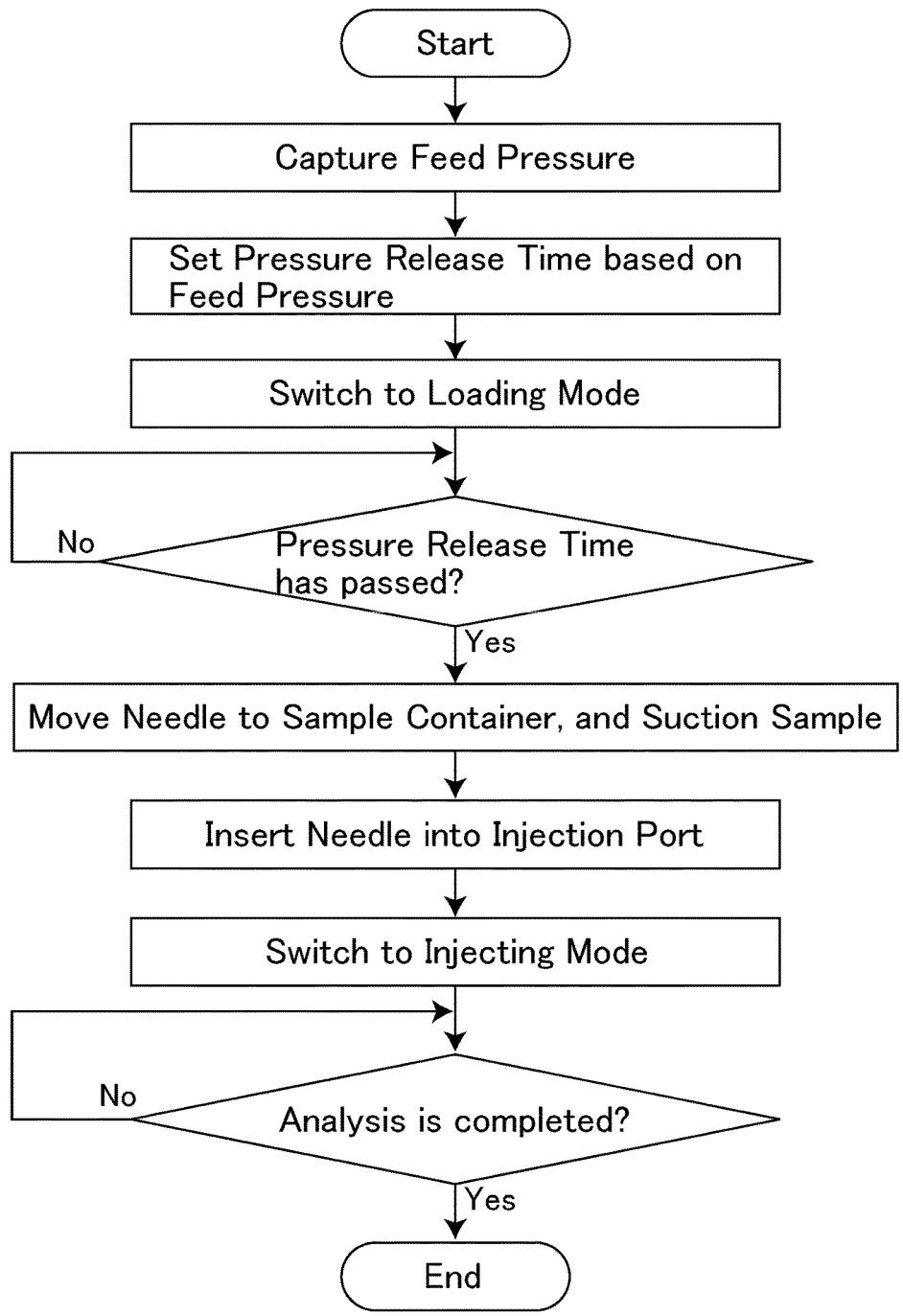
FIG. 4 is a flowchart showing an operation according to the embodiment.

Next, an example of the operation of the embodiment will be described with reference to FIGS. 1, 2, 5 and 6, and the flowchart in FIG. 4.

Before execution of the sampling operation, the needle 16 is inserted in the injection port "d", and the first switching valve 2 is in the injecting mode (this state is referred to as a standby state). When the control unit 42 of the autosampler 1 receives a signal for sampling operation start from the system controller 48, the control unit 42 captures information about the feed pressure of the feeding device 19, and sets the pressure release time based on the feed pressure and the pressure release time information held in the pressure release time information holding unit 47.

After the pressure release time is set, the first switching valve 2 is switched to the loading mode, and the sampling channel 10 and the syringe channel 12 are connected, and also, the second switching valve 4 is placed in a state where the ports "g" and "k" are connected (see FIG. 5), and standby is performed until lapse of the pressure release time is set. The pressure inside the sampling channel 10 is thereby returned to atmospheric pressure.

Figure 6:
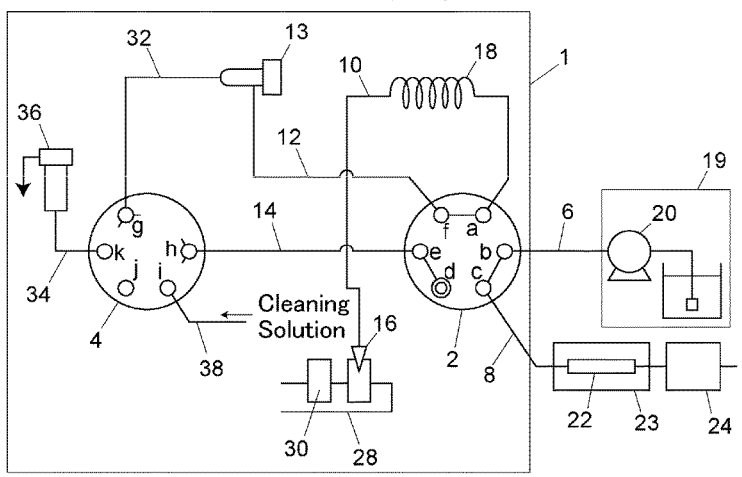
FIG. 6 is a channel configuration diagram at the time of a sampling operation according to the embodiment.

After the pressure release operation is ended, the second switching valve 4 is switched to a state where the ports "g" and "k" are cut off from each other, and the needle 16 is moved to the position of a predetermined sample container 30, and the tip end is inserted to suction the sample (see FIG. 6). After the sample is suctioned, the needle 16 is inserted in the injection port "d", and the first switching valve 2 is switched to the injecting mode (See FIG. 1), and a sample retained in the sample loop 18 is introduced into the analysis channel 8 by a mobile phase from the feeding device 19. The sample which is introduced into the analysis channel 8 is separated into components at the analytical column 22, and detection is performed by the detector 24. A series of operations for one sample, from sampling to analysis of the sample, is thereby ended.

In the case of cleaning inner and outer surfaces of the needle 16 after completion of separation and analysis of the sample at the analysis channel 8, the first switching valve 2 is switched again to the loading mode, and the needle 16 is moved to the cleaning port 36 so as to have the inner and outer surfaces of the needle 16 cleaned. When pulling out the needle 16 from the injection port "d", the pressure release operation has to be performed for the sampling channel 10, in the same manner as immediately before the sampling operation. After the inner and outer surfaces of the needle 16 have been cleaned, the needle 16 is again inserted into the injection port "d", and the first switching valve 2 is switched to the injecting mode to return to the standby state (see FIG. 1).

What is claimed is:

1. An autosampler comprising:
   a sampling channel including, at one end, a needle for suctioning a sample from a sample container containing a sample, and including a sample loop for retaining the sample suctioned through the needle;
   a needle drive mechanism for moving the needle;
   an injection port that is connected to the sampling channel by insertion of a tip end of the needle;
   a switching mechanism for switching, when the tip end of the needle is inserted in the injection port, to one of a state where the sampling channel is disposed between a feeding device for feeding a mobile phase and an analytical column for separating a sample into components and a state where the sampling channel is not disposed between the feeding device and the analytical column, and for switching, in a state where the sampling channel is not disposed between the feeding device and the analytical column, a system including the sampling channel between an open system and a closed system;
   a pressure release operation unit for performing, by controlling operation of the needle drive mechanism and the switching mechanism, before the tip end of the needle is pulled out from the injection port following a state where the sampling channel is disposed between the feeding device and the analytical column, a pressure release operation of switching the switching mechanism in such a way that the sampling channel is not disposed between the feeding device and the analytical column and the system including the sampling channel is made the open system, and of performing standby until a pressure inside the sampling channel is returned to atmospheric pressure; and
   a pressure release time setting unit for setting an execution time of the pressure release operation based on a feed pressure of the feeding device immediately before execution of the pressure release operation, wherein the pressure release operation unit performs the pressure release operation for a period of time set by the pressure release time setting unit.

2. The autosampler according to claim 1, further comprising a pressure release time information holding unit holding pressure release time information specifying in advance a relationship between a feed pressure and the execution time of the pressure release operation,
wherein the pressure release time setting unit captures the feed pressure of the feeding device before the pressure release operation is performed, and sets the execution time based on the captured feed pressure and the pressure release time information held in the pressure release time information holding unit.

3. The autosampler according to claim 1, comprising:
a control unit for controlling the needle drive mechanism and the switching mechanism; and
a system controller for communicating information with the control unit,
wherein the pressure release time setting unit is provided in the system controller.

4. The autosampler according to claim 2, comprising:
a control unit for controlling the needle drive mechanism and the switching mechanism; and
a system controller for communicating information with the control unit,
wherein the pressure release time setting unit is provided in the system controller.

5. The autosampler according to claim 1, wherein the switching mechanism includes
a first switching valve including a sampling port to which another end of the sampling channel is connected, a syringe port to which a syringe pump for performing suction and discharge of liquid is connected, the injection port, a mobile phase supply port to which the feeding device for feeding a mobile phase is connected, and an analysis port to which a channel communicating with the analytical column is connected, the first switching valve being for switching between a loading mode in which the sampling port and the syringe port are connected and the mobile phase supply port and the analysis port are connected, and an injecting mode in which the sampling port and the mobile phase supply port are connected and the injection port and the analysis port are connected, and
a second switching valve for switching a system including the sampling channel that is formed when the tip end of the needle is inserted in the injection port and the first switching valve is in the loading mode, between an open system and a closed system.

* * * * *